US011266365B2

(12) United States Patent
Dirisio et al.

(10) Patent No.: US 11,266,365 B2
(45) Date of Patent: Mar. 8, 2022

(54) POLYMER MAGNETIC BRAKING SYSTEM AND METHOD

(71) Applicant: CARESTREAM HEALTH, INC., Rochester, NY (US)

(72) Inventors: Anthony Dirisio, Rochester, NY (US); Adam D. Pruyne, Webster, NY (US)

(73) Assignee: Carestream Health, Inc., Rochester, NY (US)

( * ) Notice: Subject to any disclaimer, the term of this patent is extended or adjusted under 35 U.S.C. 154(b) by 144 days.

(21) Appl. No.: 16/683,535

(22) Filed: Nov. 14, 2019

(65) Prior Publication Data

US 2020/0155090 A1    May 21, 2020

Related U.S. Application Data

(60) Provisional application No. 62/769,055, filed on Nov. 19, 2018, provisional application No. 62/769,011, filed on Nov. 19, 2018.

(51) Int. Cl.
*A61B 6/00* (2006.01)
*F16D 69/02* (2006.01)
*F16D 121/18* (2012.01)

(52) U.S. Cl.
CPC .......... *A61B 6/4405* (2013.01); *A61B 6/4452* (2013.01); *F16D 69/02* (2013.01); *A61B 6/447* (2013.01); *F16D 2121/18* (2013.01)

(58) Field of Classification Search
CPC ..... A61B 6/105; A61B 6/4405; A61B 6/4452; A61B 6/447; A61B 6/4476; F16D 69/02; F16D 2121/18
See application file for complete search history.

(56) References Cited

U.S. PATENT DOCUMENTS

| 4,964,152 | A | 10/1990 | Kaul et al. | |
|---|---|---|---|---|
| 8,465,203 | B2 | 6/2013 | Barker et al. | |
| 8,876,379 | B2 * | 11/2014 | DiRisio | A61B 6/447 378/198 |
| 2003/0217901 | A1 * | 11/2003 | Carlson | F16F 15/03 188/267 |
| 2016/0069439 | A1 * | 3/2016 | Davies | F16F 15/03 74/89.39 |
| 2020/0155083 | A1 | 5/2020 | DiRisio | |
| 2020/0155090 | A1 | 5/2020 | DiRisio | |
| 2020/0155091 | A1 | 5/2020 | DiRisio | |

* cited by examiner

*Primary Examiner* — Dani Fox

(57) ABSTRACT

A mobile radiography system includes a wheeled transport frame and a vertical column mounted on the transport frame. A telescoping arm is attached to the vertical column and to an x-ray tube head. The telescoping arm includes a first section, a second section movable within the first section, and a third section movable within the second section. The first section and the second section each include a drag assembly configured to provide a drag force on the linearly movable section therewithin. The drag assemblies each include a friction material pressed against the linearly movable section to provide a constant drag force on the linearly movable section while it moves. A permanent pressure source presses the friction material against the linearly movable section.

18 Claims, 5 Drawing Sheets

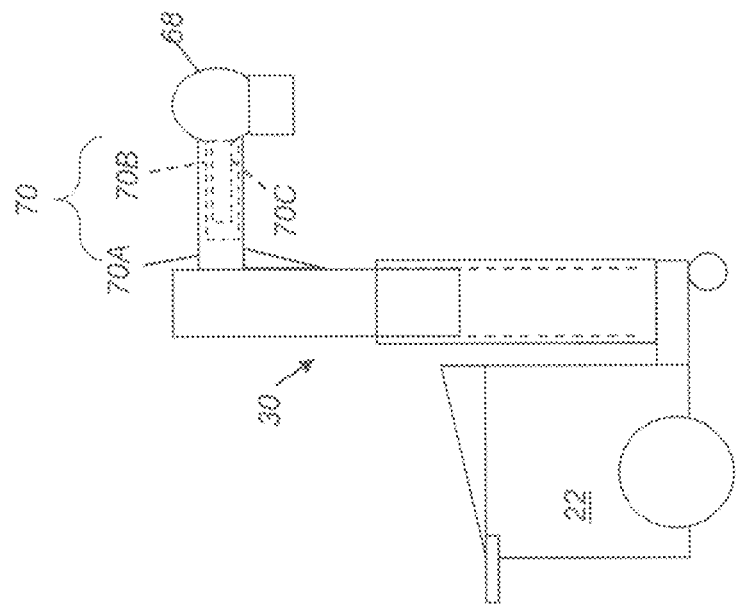
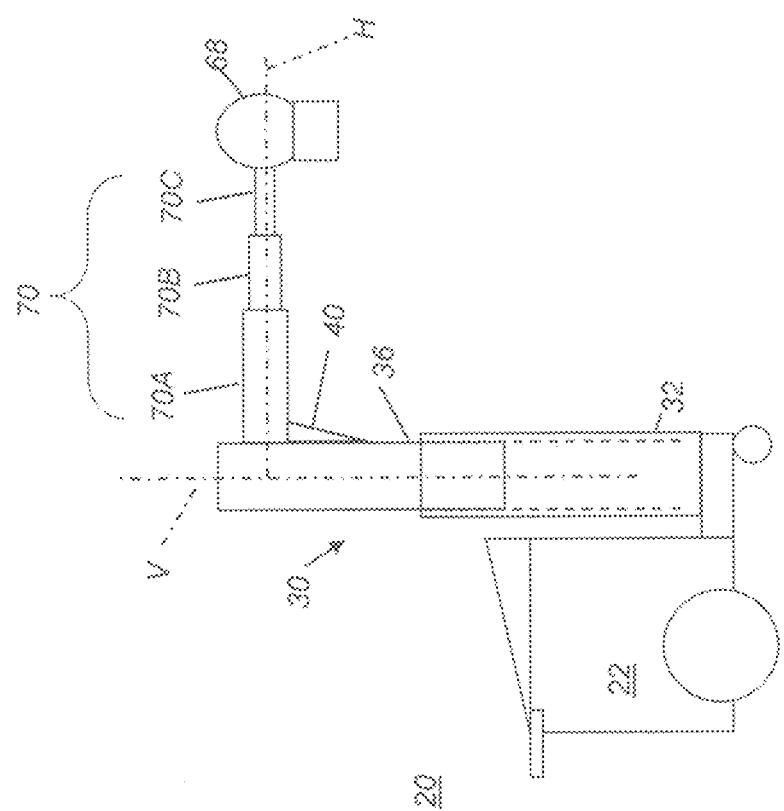

POLYMER MAGNETIC BRAKING SYSTEM AND METHOD

CROSS REFERENCE TO RELATED APPLICATIONS

This application claims priority to U.S. Patent Application Ser. No. 62/769,055, filed Nov. 19, 2018, in the name of Dirisio et al., and entitled BRAKING SYSTEM AND METHOD, which is hereby incorporated by reference herein in its entirety.

This application claims priority to U.S. Patent Application Ser. No. 62/769,011, filed Nov. 19, 2018, in the name of Spaeth et al., and entitled COLLIMATOR KNOBS AND POLYMER MAGNETIC BRAKE, which is hereby incorporated by reference herein in its entirety.

This application is related in certain respects to U.S. Pat. No. 8,876,379 B2, filed Apr. 11, 2011, in the name of Dirisio et al., and entitled COLLAPSIBLE COLUMN MOVEMENT APPARATUS FOR MOBILE X-RAY DEVICE, which is hereby incorporated by reference herein in its entirety.

BACKGROUND OF THE INVENTION

The invention relates generally to the field of medical imaging, and in particular to portable radiographic imaging apparatus. More specifically, the invention relates to a mobile radiography apparatus including improved operational features.

Mobile carts are employed in medical facilities to move medical equipment between locations. One type of mobile cart includes an x-ray source used to capture digital x-ray images in a digital radiographic detector. Mobile x-ray apparatus are of particular value in intensive care apparatus (ICU) and other environments where timely acquisition of a radiographic image is important. Because portable carts can be wheeled around the ICU or other area and brought directly to the patient's bedside, a portable x-ray imaging apparatus allows an attending physician or clinician to have recent information on the condition of a patient and helps to reduce the risks entailed in moving patients to stationary equipment in the radiological facility.

The discussion above is merely provided for general background information and is not intended to be used as an aid in determining the scope of the claimed subject matter.

BRIEF DESCRIPTION OF THE INVENTION

A mobile radiography system includes a wheeled transport frame and a vertical column mounted on the transport frame. A telescoping arm is attached to the vertical column and to an x-ray tube head. The telescoping arm includes a first section, a second section movable within the first section, and a third section movable within the second section. The first section and the second section each include a drag assembly configured to provide a drag force on the linearly movable section therewithin. The drag assemblies each include a friction material pressed against the linearly movable section to provide a constant drag force on the linearly movable section while it moves. A permanent pressure source presses the friction material against the linearly movable section.

In one embodiment, a mobile radiography system includes a transport frame having wheels attached thereto for rollably transporting the system, a vertical column mounted on the transport frame, and a telescoping boom attached to the vertical column. An x-ray tube head is attached to the telescoping boom for adjusting a position of the tube head in any of three dimensions. The telescoping boom includes a linearly movable portion and a drag assembly configured to provide a constant drag force on the linearly movable portion. A friction material is pressed against the linearly movable portion continuously to provide the drag force and a pressing source, such as a magnet, presses the friction material against the movable portion.

In another embodiment, a brake assembly includes a movable portion and a drag portion configured to provide a drag force on the movable portion. The drag portion includes a friction material pressed against the movable portion continuously to provide a constant drag force on the movable portion. A pressing source constantly presses the friction material against the movable portion.

In another embodiment, a radiography system includes an x-ray source and a telescoping arm attached to the x-ray source for supporting, and allowing variable positioning of, the x-ray source. The telescoping arm includes at least a linear first section, a linear second section movable within the first section, and a linear third section movable within the linear second section. The first section and the second section each include a drag assembly configured to provide a drag force on the linearly movable section therewithin. Each drag assembly includes a friction material configured to be continuously pressed against the linearly movable section therewithin to provide a constant drag force while the linearly movable section is moving. A constant pressing source in each drag assembly presses the friction material against the linearly movable section.

The summary descriptions above are not meant to describe individual separate embodiments whose elements are not interchangeable. In fact, many of the elements described as related to a particular embodiment can be used together with, and possibly interchanged with, elements of other described embodiments. Many changes and modifications may be made within the scope of the present invention without departing from the spirit thereof, and the invention includes all such modifications.

This brief description of the invention is intended only to provide a brief overview of subject matter disclosed herein according to one or more illustrative embodiments, and does not serve as a guide to interpreting the claims or to define or limit the scope of the invention, which is defined only by the appended claims. This brief description is provided to introduce an illustrative selection of concepts in a simplified form that are further described below in the detailed description. This brief description is not intended to identify key features or essential features of the claimed subject matter, nor is it intended to be used as an aid in determining the scope of the claimed subject matter. The claimed subject matter is not limited to implementations that solve any or all disadvantages noted in the background.

BRIEF DESCRIPTION OF THE DRAWINGS

So that the manner in which the features of the invention can be understood, a detailed description of the invention may be had by reference to certain embodiments, some of which are illustrated in the accompanying drawings. It is to be noted, however, that the drawings illustrate only certain embodiments of this invention and are therefore not to be considered limiting of its scope, for the scope of the invention encompasses other equally effective embodiments. The drawings below are intended to be drawn neither to any precise scale with respect to relative size, angular relationship, relative position, or timing relationship, nor to any combinational relationship with respect to interchangeability, substitution, or representation of a required implementation, emphasis generally being placed upon illustrating the features of certain embodiments of the invention. In the drawings, like numerals are used to indicate like parts throughout the various views. Thus, for further understanding of the invention, reference can be made to the following detailed description, read in connection with the drawings in which:

FIGS. 2A-2D are schematic side views of the mobile radiography apparatus of FIG. 1;

DETAILED DESCRIPTION OF THE INVENTION

Figure 1:
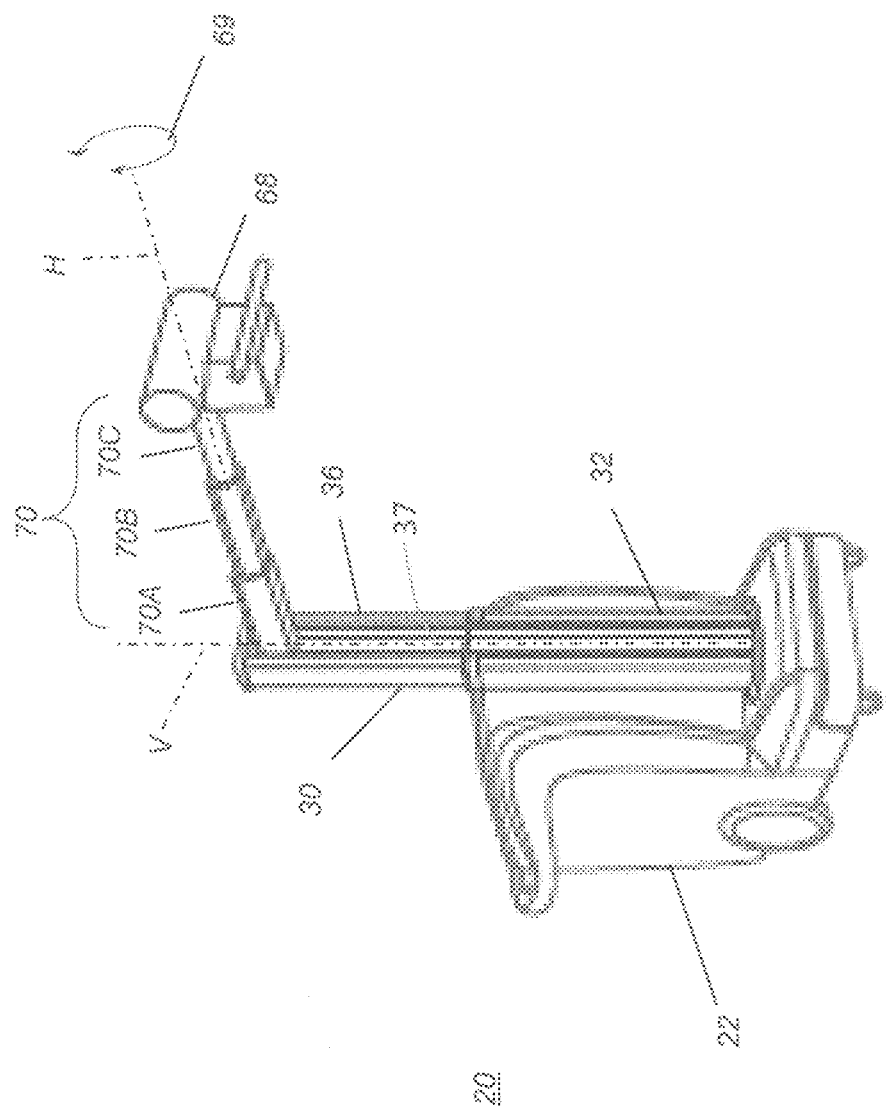
FIG. 1 is a perspective view of a mobile radiography apparatus.

With reference to FIG. 1 a mobile radiography apparatus 20 includes a telescoping boom 70 coupled to a telescoping, sectioned vertical column 30 according to one embodiment. An x-ray tube head 68 is in position for imaging, extended from vertical column 30, and supported, by boom 70 along a horizontal axis H that may be perpendicular, or slightly angled, relative to the vertical axis V. The mobile radiography apparatus 20 has a wheeled transport frame 22. Telescoping sectioned vertical column 30 is mounted on frame 22 parallel to the vertical axis V and has a vertically stationary base section 32 that seats against the frame 22. At least one movable section 36 of the vertical column 30 is vertically translatable within the stationary base section 32 to extend along the vertical axis V, so that boom 70 and x-ray tube head 68 can be set to a suitable height over a range of possible height settings. Boom 70 includes three tubular boom sections 70A, 70B, 70C, each having a relatively decreasing cross sectional area, respectively. The boom section 70C, having the smallest cross sectional area, is rotatably attached to the x-ray tube head 68, to allow the tube head 68 to rotate about axis H, as indicated by double headed arrow 69. Boom section 70A, having the largest cross sectional area, is attached to the vertical column 30 by boom support frame 40 (FIG. 3) to allow height adjustment of the boom 70 along a vertical track 37 in the vertical column 30. Boom section 70A is not horizontally adjustable so that it remains in a fixed horizontal position relative to column 30. Boom section 70B is movable relative to boom section 70A by sliding into or out of boom section 70A parallel to horizontal axis H. Boom section 70C is movable relative to boom section 70A and boom section 70B by sliding into or out of boom section 70B parallel to horizontal axis H.

Figure 2D:
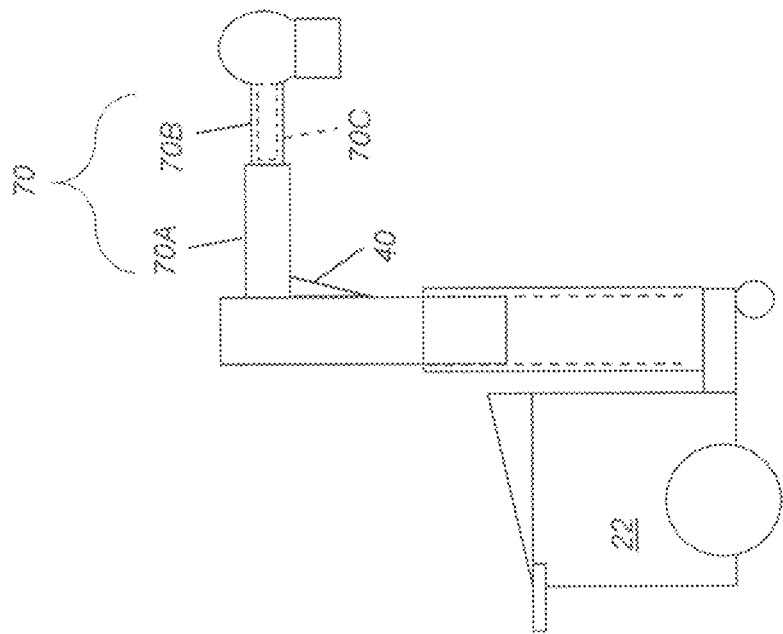
Figure 2C:
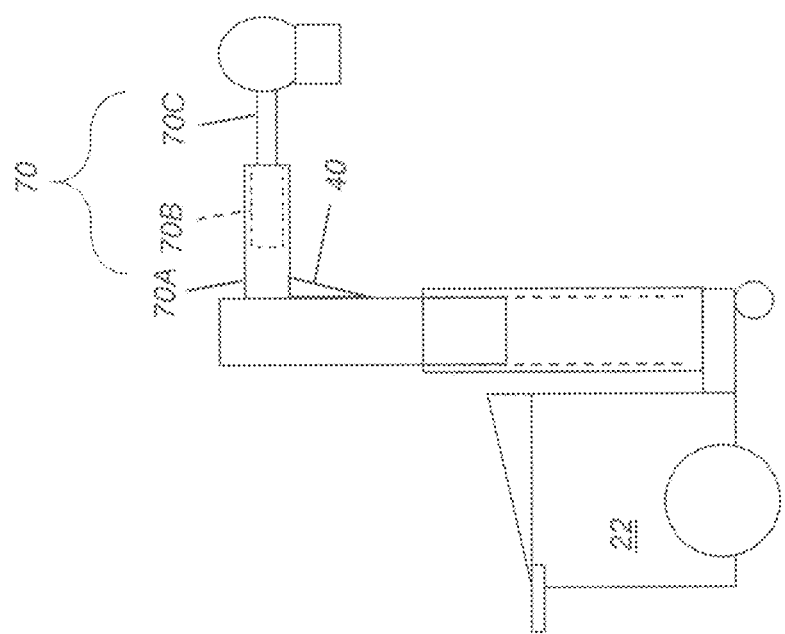

Embodiments of the present invention use a boom brake assembly (FIG. 4) that cooperates mechanically within the telescoping boom 70 to allow horizontal displacement of the x-ray tube head 68 over a wide range of horizontal positions as described herein. An operator can easily adjust a height of the boom 70 along vertical column 30 and a horizontal distance of the x-ray tube head 68 from the vertical column 30. As shown in FIG. 2A, stationary base section 32 may include a hollow cavity or shaft allowing movable section 36 to travel vertically therethrough. The boom 70 may be raised to a height near the top of movable section 36 while movable section 36 is extended vertically within the shaft of stationary base section 32. As shown in FIG. 2B, the boom 70 may be collapsed to its shortest length by manually urging the tube head 68 toward the vertical column 30 so that boom section 70B slides into boom section 70A and boom section 70C slides into boom section 70B. FIG. 2C-2D illustrate optional movement capabilities of the boom sections 70B, 70C. In FIG. 2C, boom section 70B is fully inserted into boom section 70A while boom section 70C is not inserted into boom section 70B. In FIG. 2D, boom section 70C is fully inserted into boom section 70B while boom section 70B is not inserted into boom section 70A. Thus, the boom sections 70B, 70C, may each be fully or partially manually inserted by sliding one or both of them into the corresponding larger boom section, as desired.

Figure 3:
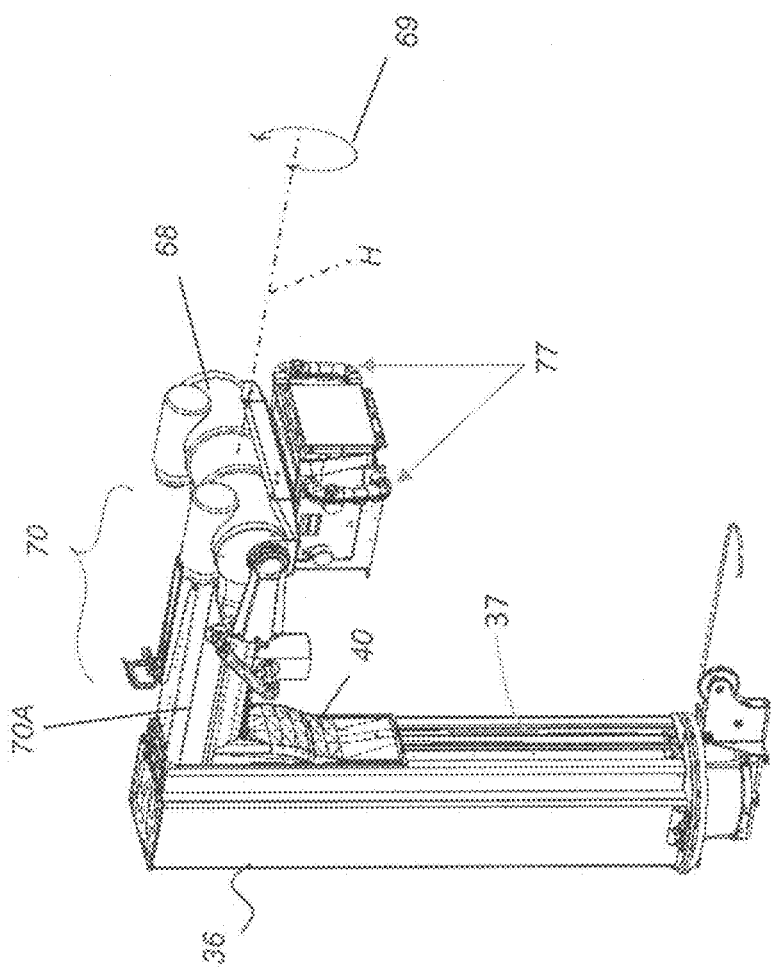
FIG. 3 is a partial perspective view of the schematic view of FIG. 2B.

FIG. 3 shows the movable upper section 36 in isolation together with boom 70 in a fully collapsed position having boom sections 70B and 70C within boom section 70A, corresponding to the same position as in FIG. 2B, x-ray tube head 68, and the boom support frame 40 that is secured to boom section 70A and to a track 37 used to raise and lower the boom 70 and x-ray tube head 68. X-ray tube head 68 may be rotated about the horizontal axis H in clockwise or counterclockwise directions 69. Handles 77 are attached to the tube head 68 to allow an operator to manually adjust a height of the tube head 68, to extend and retract the tube head away and toward the vertical column 30 by operation of the boom 70 as described herein, and to rotate the tube head 68 about a horizontal axis H.

It is beneficial to allow the fullest possible range of vertical heights for the x-ray source in a portable system, from above shoulder height of the imaging technician to relatively low elevations, such as might be beneficial for imaging the foot or ankle of a patient. Applicants have noted that during the operations of extending and retracting the boom 70 there can be an improvement in the operation. For example, reducing noise, so as to not interfere or adversely affect the comfort of the patient and medical technician or improving smoothness of the operation so as to improve the usability and ease of comfort of the medical technician.

Applicants have developed a brake assembly to improve the operation of the mobile radiography apparatus 20. One benefit is to eliminate/reduce noise which may occur during extending and retracting the boom 70. The boom 70 and the components employed to extend/retract the boom 70 have many contact points that slide against and contact each other during operation. Applicants' brake assembly, as described herein, mitigates undesirable noise issues.

Figure 4:
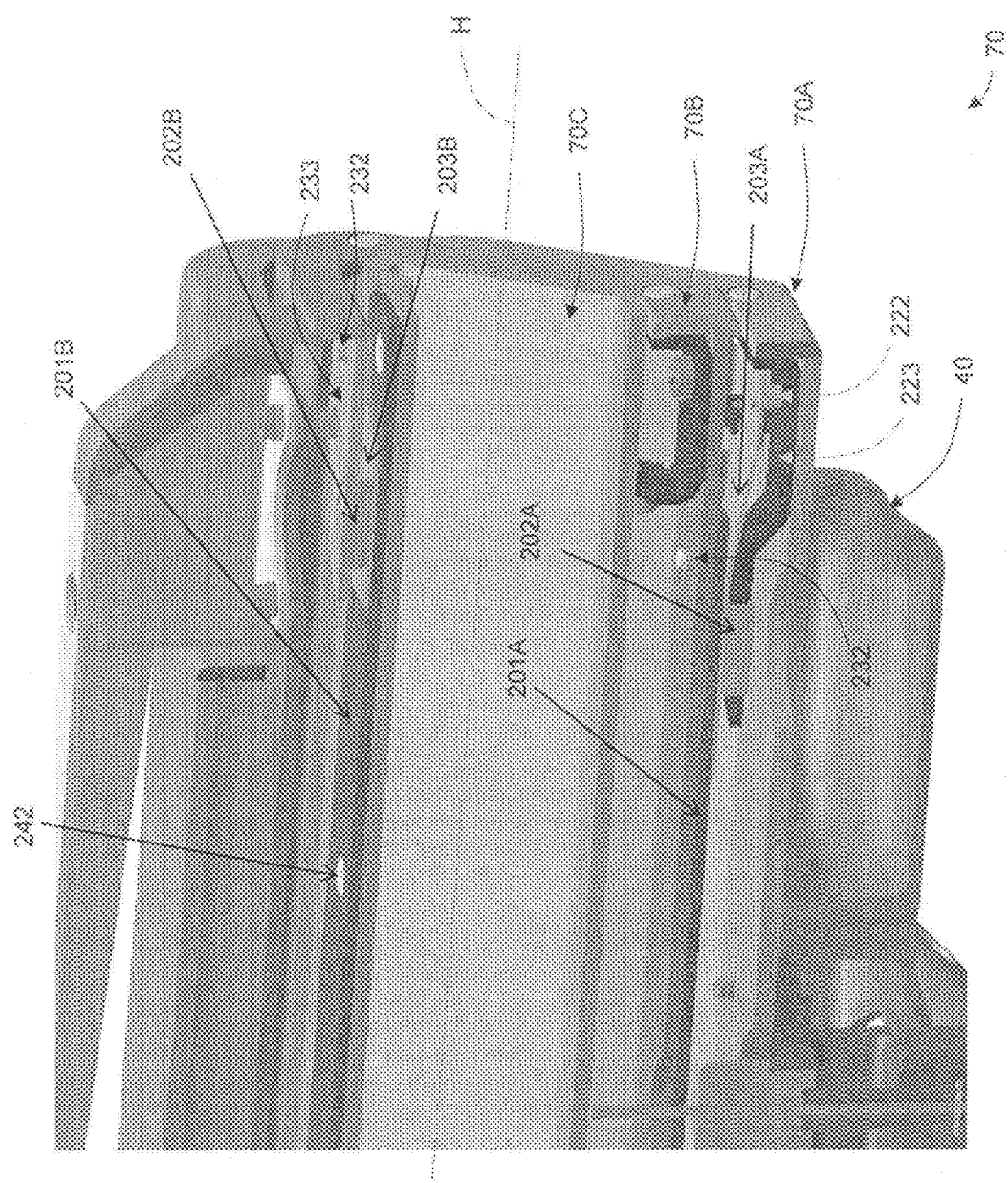
FIG. 4 is cross section view of an end portion of the boom.

FIG. 4 illustrates a cross section of boom 70 at a terminal end thereof where the tube head 68 is attached. The boom 70 includes a polymer magnetic brake assembly including brake plates 201A, 201B, magnets 202A, 202B, and polymer friction material 203A, 203B. The brake plate 201A, magnet 202A, and polymer friction material 203A may be considered as part of boom section 70A used to control sliding movement of boom section 70B therewithin, parallel to horizontal axis H. The brake plate 201B, magnet 202B, and polymer friction material 203B may be considered as part of boom section 70B used to control sliding movement of boom section 70C therewithin, parallel to horizontal axis H. In one embodiment, the magnets 202A, 202B, may be made from neodymium, an alloy of neodymium, iron and boron (NdFeB), and the polymer material 203A, 203B, may be made from Ultra High Molecular Weight Polyethylene (UHMWPE). Typical brake assemblies suffer from frictional material wear which causes changes in frictional force over time. The frictional wear may also create dust and debris. UHMWPE was selected for a friction material because of its low coefficient of friction and its superior wear properties. The coefficient of friction provided by the polymer material 203A, 203B, may require a normal force provided by the magnets 202A, 202B, to hold the polymer material 203A, 203B, against the brake plates 201A, 201B. There are no moving parts or adjustments required in this type of brake assembly.

As shown in the example embodiment of FIG. 4, the boom 70 includes a linearly extendable and retractable tubular design as shown. A boom support frame 40 may be used to support the boom 70 in a substantially horizontal position. The boom 70 includes tubular sections 70A, 70B, 70C. Tubular section 70A may be a stationary section with respect to boom support frame 40, being fixably secured thereto. Tubular section 70B may be configured to travel parallel to longitudinal axis H by sliding within tubular stationary section 70A and relative to tubular section 70C. Tubular section 70B may have a brake plate 201A secured thereto using one or more screws 232 along its length. Stationary section 70A may include a bracket 223 secured thereto which includes a cutout portion to hold magnet 202A in position to prevent the magnet 202A from traveling with section 70B when section 70B moves parallel to longitudinal axis H. Frictional material 203A is positioned between magnet 202A and brake plate 201A and is secured in place by a fastener 222 secured to the frictional material 203A and to bracket 223. Brake plate 201A is made from a material to which magnet 202A is attracted. Magnet 202A is free to move in a direction normal to brake plate 201A and is separated therefrom by a thickness of frictional material 203A, thereby pressing the frictional material 203A against brake plate 201A to provide a constant drag force against movement of section 70B relative to stationary section 70A. The drag force provided is not sufficient to prevent sliding movement of section 70B relative to stationary section 70A, such as by an operator's manual urging thereof, but may be sufficient to hold section 70B in place relative to section 70A to prevent unintended movement caused by, for example, gravitational force, vibrations or bumping.

Tubular section 70C may be configured to travel parallel to longitudinal axis H by sliding within tubular section 70B and relative to stationary tubular section 70A. Tubular section 70C may have a brake plate 201B secured thereto using one or more screws 242 along its length. Tubular section 70B may include a bracket 233 secured thereto which includes a cutout portion to hold magnet 202B in position to prevent the magnet 202B from traveling with section 70C when section 70C moves parallel to longitudinal axis H. Frictional material 203B is positioned between magnet 202B and brake plate 201B and is secured in place by a fastener 232 secured to the frictional material 203B and to bracket 233. Brake plate 201B is made from a material to which magnet 202B is attracted. Magnet 202B is free to move in a direction normal to brake plate 201B and is separated therefrom by a thickness of frictional material 203B, thereby pressing the frictional material 203B against brake plate 201B to provide a constant drag force against movement of section 70C relative to section 70B. The drag force provided is not sufficient to prevent sliding movement of section 70C relative to section 70B, such as by an operator's manual urging thereof, but may be sufficient to hold section 70C in place relative to section 70B to prevent unintended movement caused by, for example, gravitational force, vibrations or bumping.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

The invention claimed is:

1. A mobile radiography system comprising:
    a transport frame having wheels attached thereto for rollably transporting the system;
    a vertical column mounted on the transport frame; and
    a telescoping boom attached to the vertical column at a first end of the telescoping boom, the telescoping boom attached to an x-ray tube head at a second end of the telescoping boom opposite the first end,
    wherein the telescoping boom comprises:
        a first tubular section;
        a second tubular section; and
        a third section, wherein the first tubular section comprises a first interior volume large enough to enclose the second tubular section, the second tubular section comprises a second interior volume large enough to enclose the third section, the second tubular section comprises a first linearly movable portion configured to move linearly within the first tubular section, and wherein the third section comprises a second linearly movable portion configured to move linearly within the second tubular section;
    a first drag assembly attached to the first tubular section configured to provide a drag force on the first linearly movable portion; and
    a second drag assembly attached to the second tubular section configured to provide a drag force on the second linearly movable portion,
    wherein the first drag assembly and the second drag assembly each comprises:
        a friction material configured to be pressed against an exterior surface of the first or second linearly movable portion continuously to provide a constant drag force on the first or second linearly movable portion while the movable portion is moved linearly; and
        a pressure source to press the friction material against the exterior surface of the first or second linearly movable portion.

2. The system of claim 1, wherein the third section comprises a linear tube or solid rod.

3. The system of claim 1, wherein the first tubular section is a stationary section.

4. The system of claim 1, wherein the friction material comprises Ultra High Molecular Weight Polyethylene.

5. The system of claim 1, wherein the pressure source comprises a magnetic material attracted to the first or second linearly movable portion, and wherein the friction material is positioned between the magnetic material and the first or second linearly movable portion.

6. The system of claim 5, wherein the magnetic material comprises neodymium.

7. A brake assembly for a telescoping assembly, the telescoping assembly comprising:
    a first portion and a second portion, the first portion configured to be linearly movable within the second portion, the second portion at least partially enclosing the first portion; and
    a third portion, the second portion configured to be linearly movable within the third portion, the third portion at least partially enclosing the second portion, wherein the brake assembly drag portion comprises:
- a first friction material attached to the second portion and configured to be frictionally pressed against an exterior surface of the first linearly movable portion continuously to provide a constant drag force on the first linearly movable portion;
- a second friction material attached to the third portion and configured to be frictionally pressed against an exterior surface of the second linearly movable portion continuously to provide a constant drag force on the second linearly movable portion; and
- a first pressure source to press the first friction material against the outside surface of the first linearly movable portion and a second pressure source to press the second friction material against the outside surface of the second linearly movable portion.

8. The brake assembly of claim 7, wherein the first portion comprises an elongated tube or solid rod.

9. The brake assembly of claim 7, wherein the third portion comprises a stationary section.

10. The brake assembly of claim 9, wherein the first and second friction material comprises Ultra High Molecular Weight Polyethylene.

11. The brake assembly of claim 10, wherein the first and second pressure source each comprises a magnetic material, and wherein the first and second friction material is positioned between the first and second pressure source and the first and second linearly movable portion, respectively.

12. The brake assembly of claim 11, wherein the magnetic material comprises neodymium.

13. A radiography system comprising:
- an x-ray source; and
- a telescoping arm mechanically attached to a support at a first end of the telescoping arm, the telescoping arm mechanically attached to the x-ray source at a second end of the telescoping arm opposite the first end,
- wherein the telescoping arm comprises at least a linear first section, a linear second section smaller than the first section and movable within an interior volume of the first section, and a linear third section smaller than the second section and movable within an interior volume of the linear second section, and wherein the first section and the second section each include a drag assembly configured to provide a drag force on the linearly movable section therewithin, and
- wherein each drag assembly comprises:
  - a friction material configured to be pressed against an exterior surface of the linearly movable section therewithin continuously to provide a constant drag force on the linearly movable section therewithin while the linearly movable section therewithin is moving; and
  - a pressure source to press the friction material against the exterior surface of the linearly movable section therewithin.

14. The system of claim 13, wherein the linear first section and the linear second section each comprises a linear tube.

15. The system of claim 14, wherein the linear third section comprises a linear tube.

16. The system of claim 13, wherein the friction material comprises Ultra High Molecular Weight Polyethylene.

17. The system of claim 13, wherein the pressure source comprises a magnetic material attracted to the linearly movable section therewithin, and wherein the friction material is positioned between the magnetic material and the linearly movable section therewithin.

18. The system of claim 17, wherein the magnetic material comprises neodymium.

* * * * *

UNITED STATES PATENT AND TRADEMARK OFFICE
CERTIFICATE OF CORRECTION

PATENT NO. : 11,266,365 B2
APPLICATION NO. : 16/683535
DATED : March 8, 2022
INVENTOR(S) : Anthony Dirisio et al.

It is certified that error appears in the above-identified patent and that said Letters Patent is hereby corrected as shown below:

In the Claims

Column 7, Claim 7, Line 1    Please replace "wherein the brake assembly drag portion comprises:" with -- wherein the brake assembly comprises: --

Signed and Sealed this
Twelfth Day of April, 2022

Drew Hirshfeld
*Performing the Functions and Duties of the
Under Secretary of Commerce for Intellectual Property and
Director of the United States Patent and Trademark Office*